United States Patent
Wada et al.

(10) Patent No.: US 8,003,814 B2
(45) Date of Patent: Aug. 23, 2011

(54) METAL ALKOXIDE COMPOUND, MATERIAL FOR FORMING THIN FILM, AND METHOD FOR PRODUCING THIN FILM

(75) Inventors: Senji Wada, Tokyo (JP); Tetsuji Abe, Tokyo (JP); Atsushi Sakurai, Tokyo (JP); Takashi Higashino, Tokyo (JP); Ryusaku Fujimoto, Tokyo (JP); Masako Shimizu, Tokyo (JP)

(73) Assignee: Adeka Corporation, Tokyo (JP)

( * ) Notice: Subject to any disclaimer, the term of this patent is extended or adjusted under 35 U.S.C. 154(b) by 1014 days.

(21) Appl. No.: 11/854,109

(22) Filed: Sep. 12, 2007

(65) Prior Publication Data

US 2008/0187662 A1    Aug. 7, 2008

(30) Foreign Application Priority Data

Sep. 15, 2006    (JP) .................. 2006-251575

(51) Int. Cl.
*C07F 7/00* (2006.01)
*C23C 16/40* (2006.01)
(52) U.S. Cl. ........................ 556/54; 106/1.25
(58) Field of Classification Search .......... 556/54; 106/1.25
See application file for complete search history.

(56) References Cited

U.S. PATENT DOCUMENTS 2,684,972 A * 7/1954 Haslam ............... 556/54
2007/0190249 A1   8/2007 Hosokawa et al.

FOREIGN PATENT DOCUMENTS

| JP | 60-258132 | 12/1985 |
|---|---|---|
| JP | 01-172390 | 7/1989 |
| JP | 5-239650 | 9/1993 |
| JP | 6-60406 | 8/1994 |
| JP | 2002-69641 | 3/2002 |
| JP | 2002-93803 | 3/2002 |
| JP | 2002-93804 | 3/2002 |
| JP | 2005-340405 | 12/2005 |
| JP | 2006-182709 | 7/2006 |
| KR | 100156980 B1 | 7/1998 |

OTHER PUBLICATIONS

S.C. Goel et al.—Methyl Butenoxy Derivatives of Various Elements, Z. anorg. allg. Chem. 447, pp. 253-256, Dec. 31, 1978.
Chinese Official Action—200710152709.3—Apr. 26, 2011.

* cited by examiner

*Primary Examiner* — Porfirio Nazario Gonzalez
(74) *Attorney, Agent, or Firm* — Young & Thompson

(57) ABSTRACT

A metal alkoxide compound represented by the following general formula (1),

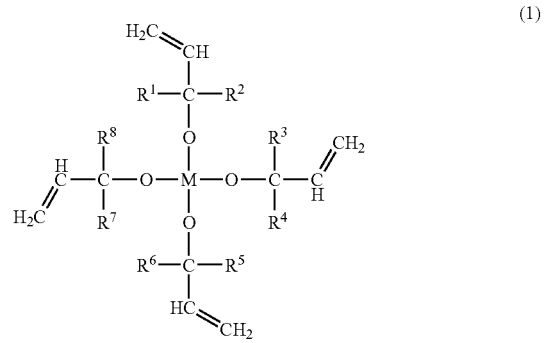

wherein each of $R^1$ to $R^8$ is independently a hydrogen atom or a methyl group; M is a titanium, a zirconium or a hafnium atom.

6 Claims, 4 Drawing Sheets

METAL ALKOXIDE COMPOUND, MATERIAL FOR FORMING THIN FILM, AND METHOD FOR PRODUCING THIN FILM

BACKGROUND OF THE INVENTION

1. Field of the Invention

The present invention relates to a metal alkoxide compound having a novel specific structure, a material for forming a thin film containing the compound, and a method for producing a thin film using the material.

2. Description of the Related Art

A thin film that contains titanium, zirconium or hafnium is used as an electronic member for electronic components such as high-dielectric capacitors, ferroelectric capacitors, gate insulating films and barrier films, or an optical member for optical communication devices such as optical wave guides, optical switches, and optical amplifiers.

As a method for producing the above thin film, there may be mentioned flame deposition, sputtering, ion plating, MOD such as coating thermal decomposition and sol-gel processes, chemical vapor deposition, or the like. Among these, chemical vapor deposition (hereinafter, may be simply referred to as "CVD") including Atomic Layer Deposition (ALD) is an appropriate production process, because of its many advantages including excellent properties in composition control and step coverage, suitability for mass production, capability of providing hybrid integration, and the like.

In the CVD process, a metal compound having organic ligands is used as a precursor supplying metal atoms source for a thin film. A compound (precursor) suitable for materials used in CVD is required to have such properties as being transportable in a liquid state upon vaporization and at transportation, having a high vapor pressure and being easy to evaporate, and being stable against heat. In addition, upon thin film deposition, the decomposition is easily progressed by thermal and/or chemical reaction. As the precursors of titanium, zirconium and hafnium, tetrakis-dialkylamide compounds and tetrakis-alkoxide compounds have been examined.

Patent Documents 1 to 4 disclose tetrakis-amide compounds. Patent Documents 5 to 7 disclose tetrakis-alkoxide compounds. Patent Document 8 discloses tetrakis-amide compounds, tetrakis-alkoxide compounds and the like. Further, in claim 1 of Patent Document 9, a metal alkoxide compound represented by $M(OR')_4$ (R' is an alkyl group or alkenyl group that has 2 to 21 carbon atoms and may be branched; and M is zirconium, hafnium or titanium) is disclosed. However, regarding the alkenyl group, no specific structure is disclosed.

Patent Document 1: Japanese Patent Laid-Open Publication No. 2002-93803
Patent Document 2: Japanese Patent Laid-Open Publication No. 2002-93804
Patent Document 3: Korean Patent No. 156980
Patent Document 4: Japanese Patent Laid-Open Publication No. 2006-182709
Patent Document 5: Japanese Patent Laid-Open Publication No. H5-239650
Patent Document 6: Japanese Patent Application Publication No. H6-60406
Patent Document 7: Japanese Patent Laid-Open Publication No. 2002-69641
Patent Document 8: Japanese Patent Laid-Open Publication No. 2005-340405
Patent Document 9: Japanese Patent Laid-Open Publication No. S60-258132

Tetrakis-dialkylamide compounds have problems in thermal stability, and have a disadvantage in stable production of thin films. Further, tetrakis-alkoxide compounds are not sufficiently decomposed on thin film deposition, and have problems in productivity.

SUMMARY OF THE INVENTION

An object of the present invention is to allow, in a thin film production process involving a vaporization step, the precursor that supplies titanium, zirconium and hafnium to a thin film to have favorable decomposition properties by heat and/or oxidation, thermal stability, vapor pressure and others that meet the requirements needed as a material for forming thin films, particularly as a material for CVD.

As a result of intensive studies, the present inventors found that the above problems were resolved by a metal alkoxide compound having a specific structure, and completed the present invention.

Namely, the present invention has achieved the above objective by providing a metal alkoxide compound represented by the following general formula (1).

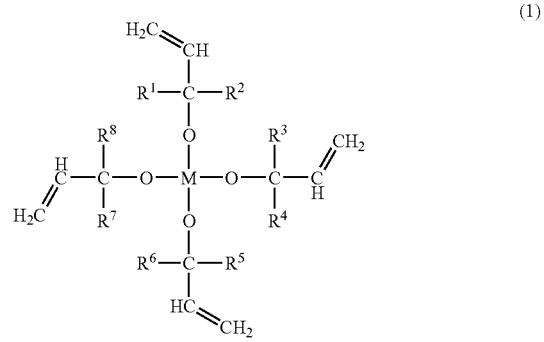

wherein each of $R^1$ to $R^8$ is independently a hydrogen atom or a methyl group; M is a titanium, a zirconium or a hafnium atom.

Further, the present invention has achieved the above objective by providing a material for forming a thin film that contains the above metal alkoxide compound.

Still further, the present invention has achieved the above objective by providing a method for producing a thin film, wherein the vapor that is obtained by vaporizing the above materials for forming a thin film and contains the metal alkoxide compound is introduced over a substrate; and the vapor is decomposed and/or chemically reacted so as to deposit a thin film on the substrate.

Still further, the present invention has achieved the above objective by providing a thin film that is deposited on a substrate by using the above method for producing a thin film.

The metal alkoxide compound of the present invention allows, in a thin film production process involving a vaporization step, the precursor that supplies titanium, zirconium and hafnium to a thin film to have favorable decomposition properties by heat and/or oxidation, thermal stability, vapor pressure and others that meet the requirements needed as a material for forming thin films, particularly as a material for CVD.

DESCRIPTION OF THE PREFERRED EMBODIMENT

Figure 1:
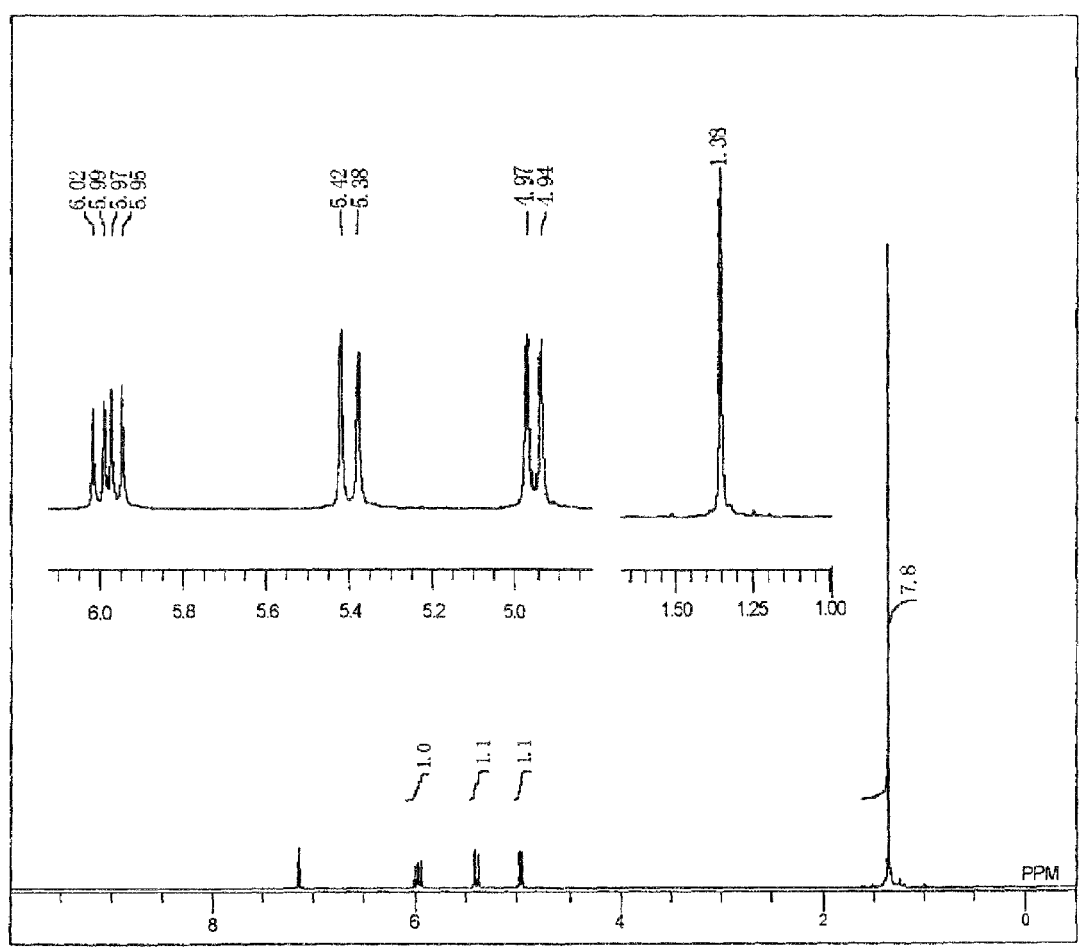
FIG. 1 shows the $^1$H-NMR chart of the metal compound (compound No. 9) of the present invention obtained in Example 1.

The metal alkoxide compound of the present invention is represented by the above general formula (1), has more favorable thermal stability compared with tetrakis-dialkylamide compounds and more favorable decomposition properties by oxidation when depositing thin films compared with tetrakis-alkoxide compounds.

Therefore, the above metal alkoxide compound is particularly suitable as a precursor for a thin film production method involving a vaporization step such as the CVD process including the ALD process.

As specific examples of the metal alkoxide compound of the present invention represented by the general formula (1), there may be mentioned the following compounds No. 1 to No. 18

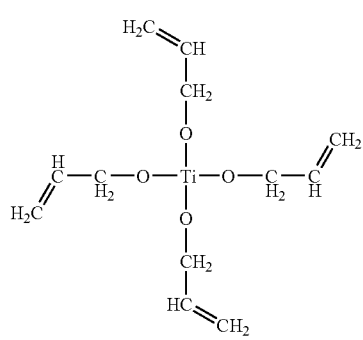

Compound No. 1

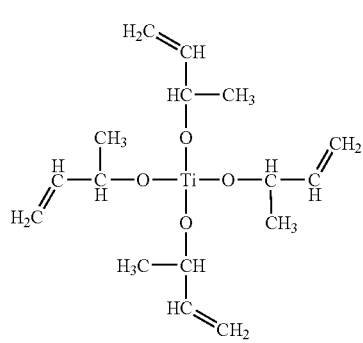

Compound No. 2

-continued

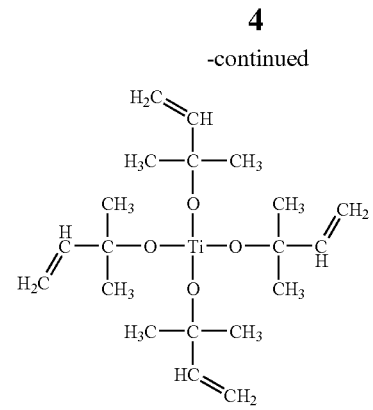

Compound No. 3

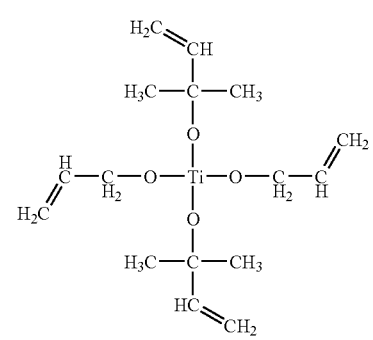

Compound No. 4

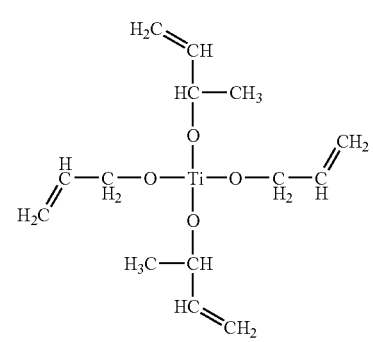

Compound No. 5

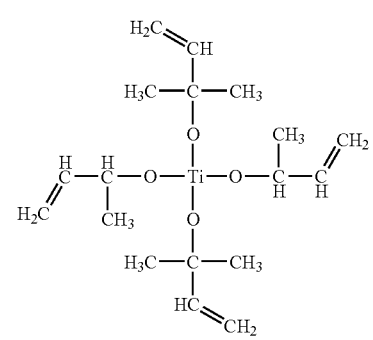

Compound No. 6

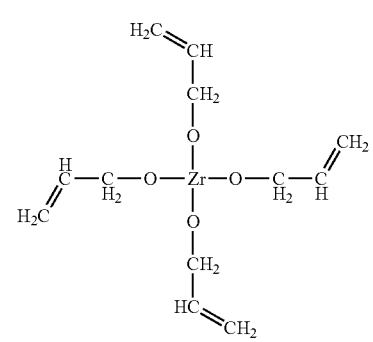

Compound No. 7

Compound No. 8
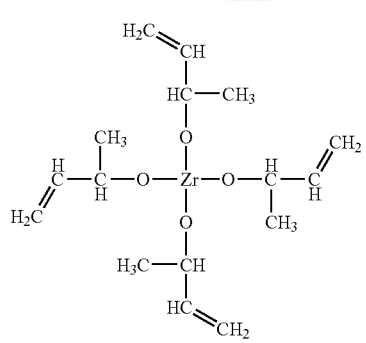
Compound No. 9
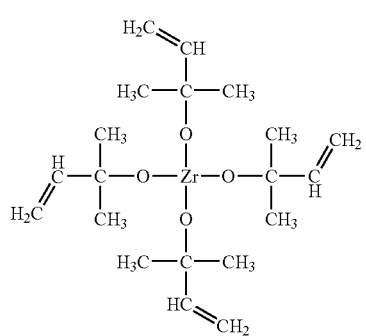
Compound No. 10
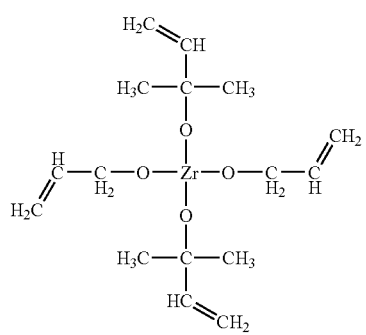
Compound No. 11
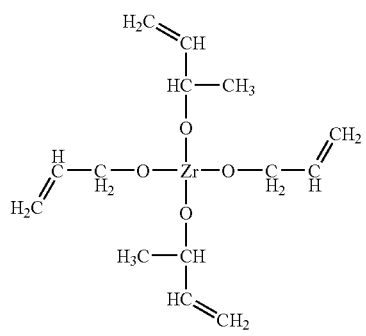
Compound No. 12
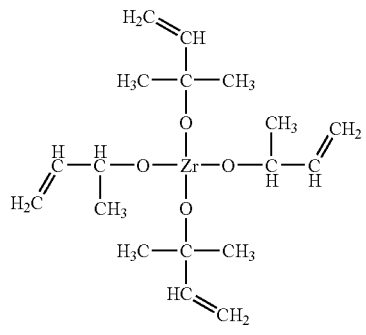
Compound No. 13
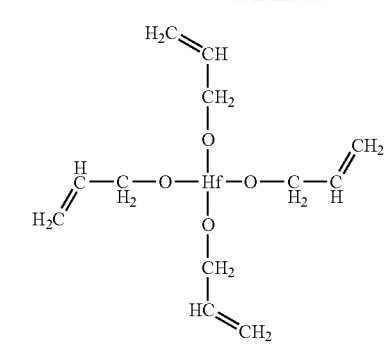
Compound No. 14
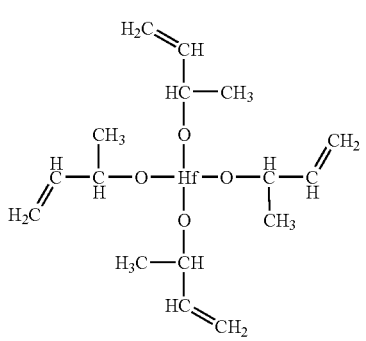
Compound No. 15
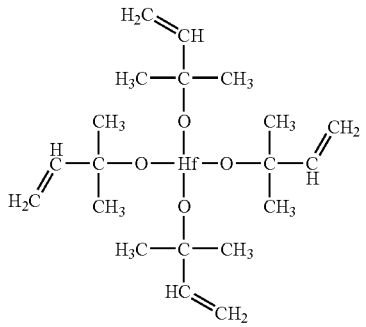
Compound No. 16
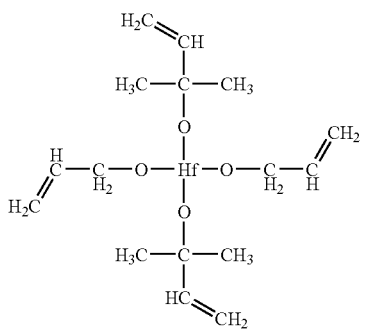
Compound No. 17

-continued

Compound No. 18

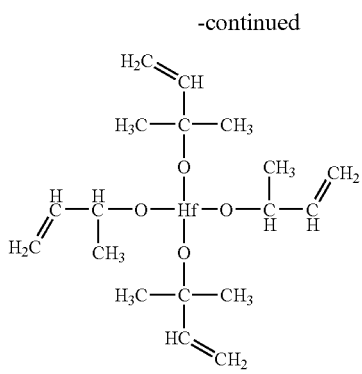

A metal alkoxide compound of the present invention that is given by substituting methyl groups for all of the $R^1$ to $R^8$ in the general formula (1) (for example, the above compounds of No. 3, No. 9 and No. 15), is particularly preferably used as a precursor for CVD or ALD because the compound has an favorable thermal stability and a high vapor pressure and is in a liquid state at room temperature.

The metal alkoxide compound of the present invention represented by the general formula (1) is not particularly limited by its production method. The metal alkoxide compound may be produced by applying known methods for synthesizing metal alkoxide compounds including (a) a method in which a metal halide such as titanium tetrachloride, zirconium tetrachloride and hafnium tetrachloride is reacted with an alcohol compound in the presence of a base such as sodium, sodium amide, and diethylamine; (b) a method in which a metal halide is reacted with an alkali metal alkoxide composed of an alkali metal and an alcohol that composes the metal alkoxide of the present invention; (c) a method by using an alcohol exchange reaction in which a metal alkoxide such as methoxide, ethoxide and isopropoxide is used as a source material; and the like.

The material for forming thin films of the present invention contains the metal alkoxide compound represented by the general formula (1) as a precursor that provides a thin film. The form and state of the material is appropriately selected depending on the process in which the material for forming thin films is used (for example, MOD such as coating thermal decomposition and sol-gel processes and CVD including ALD). The material for forming thin films of the present invention is suitably used, considering the properties of the metal alkoxide compound represented by the general formula (1), as a material for the CVD that includes a step of vaporizing the precursor, and is particularly suitably used for the production of a thin film containing metal oxides obtained by reacting the vaporized precursor with a reactive gas containing oxygen and/or ozone.

Where the material for forming a thin film of the present invention is a material for the process of chemical vapor deposition (CVD), the form and state is appropriately selected depending on the method such as a transport and supply method used in the CVD process.

As the above mentioned transport and supply method, there may be mentioned a gas carrier method in which a material for CVD is vaporized in a container of the material by heating and/or reducing pressure; the resulting vapor is introduced, if necessary with a carrier gas such as argon, nitrogen and helium, into a reaction site for film deposition; and a liquid carrier method in which a material for CVD is transported in a liquid or solution state to a vaporization chamber; the material is vaporized in the chamber by heating and/or reducing pressure; and the resulting vapor is introduced into a reaction site for film deposition.

In the gas carrier method, the metal alkoxide compound itself represented by the general formula (1) is used as the material for CVD; in the liquid carrier method, the metal alkoxide compound itself represented by the general formula (1) or a solution dissolving the metal alkoxide compound in an organic solvent is used as the material for CVD.

In a multi-component CVD process in which a multi-component thin film is produced, there are a process of vaporizing and supplying separately each material for CVD (hereinafter, may be referred to as "cocktail source process"), and a process of vaporizing and supplying a mixed material that is preliminary prepared by mixing multi components in a predetermined composition (hereinafter, may be referred to as "single source process"). In the single source process, the material for CVD is selected from a mixture of only the metal compound represented by the general formula (1), or a mixed solution dissolving the foregoing mixture in an organic solvent; and a mixture of the metal compound represented by the general formula (1) and the other precursors, or a mixed solution dissolving the foregoing mixture in an organic solvent.

There is no particular limitation on the organic solvent used in the aforementioned material for CVD, but any organic solvent generally known may be used. The organic solvent may include, for example, acetates such as ethylacetate, butylacetate and methoxyethylacetate; ethers such as tetrahydrofuran, tetrahydropyran, morpholine, ethyleneglycol dimethylether, diethyleneglycol dimethylether, triethyleneglycol dimethylether, dibutylether and dioxane; ketones such as methylbutylketone, methylisobutylketone, ethylbutylketone, dipropylketone, diisobutylketone, methylamylketone, cyclohexanone and methylcyclohexanone; hydrocarbons such as hexane, cyclohexane, methylcyclohexane, dimethylcyclohexane, ethylcyclohexane, heptane, octane, toluene and xylene; hydrocarbons having a cyano group such as 1-cyanopropane, 1-cyanobutane, 1-cyanohexane, cyanocyclohexane, cyanobenzene, 1,3-dicyanopropane, 1,4-dicyanobutane, 1,6-dicyanohexane, 1,4-dicyanocyclohexane and 1,4-dicyanobenzene; pyridine; and lutidine. These solvents are used solely or as a mixed solvent of two or more kinds depending on the solubility of the solute, the relation between the service temperature and the boiling and flash points, and the like. These solvents are used in such a manner that the total concentration of the precursors in the organic solvent is preferably from 0.01 to 2.0 mol/L and particularly preferably from 0.05 to 1.0 mol/L.

Further, in the multi-component CVD process using a cocktail source or a single source process, there are no particular limitations on the other precursors used with the metal alkoxide compound of the present invention represented by the general formula (1), but any one of generally known precursors for CVD material can be employed.

As the foregoing other precursors, there may be mentioned an organic coordination compound composed of one kind or two or more kinds of compounds selected from the group consisting of the compounds that are used as an organic ligand such as alcohol compounds, glycol compounds, β-diketone compounds, cyclopentadiene compounds and organic amine compounds, and silicon, boron, phosphorus or metal. The metal may include a Group 1 element such as lithium, sodium, potassium, rubidium and cesium; a Group 2 element such as beryllium, magnesium, calcium, strontium and barium; a Group 3 element such as scandium, yttrium, lanthanide elements (lanthanum, cerium, praseodymium, neodymium, promethium, samarium, europium, gadolinium, terbium, dysprosium, holmium, erbium, thulium, ytterbium, and lutetium) and actinoid elements; a Group 4 element such as titanium, zirconium and hafnium; a Group 5 element such as vanadium, niobium and tantalum; a Group 6 element such as chromium, molybdenum and tungsten; a Group 7 element such as manganese, technetium and rhenium; a Group 8 element such as iron, ruthenium and osmium; a Group 9 element such as cobalt, rhodium and iridium; a Group 10 element such as nickel, palladium and platinum; a Group 11 element such as copper, silver and gold; a Group 12 element such as zinc, cadmium and mercury; a Group 13 element such as aluminum, gallium, indium and thallium; a Group 14 element such as germanium, tin and lead; a Group 15 element such as arsenic, antimony and bismuth; and a Group 16 element such as polonium.

As the aforementioned other precursors, a compound having similar thermal and/or chemical decomposition behaviors is preferable for the cocktail source process. A compound causing no chemical alteration during mixing in addition to having similar thermal and/or chemical decomposition behaviors is preferable for the single source process.

The material for CVD of the present invention may contain optionally a nucleophilic reagent in order to impart stability to the metal alkoxide compound of the present invention and the other precursors. The nucleophilic reagent includes ethyleneglycol ethers such as glyme, diglyme, triglyme and tetraglyme; crown ethers such as 18-crown-6, dicylohexyl-18-crown-6, 24-crown-8, dicylohexyl-24-crown-8, and dibenzo-24-crown-8; polyamines such as ethylenediamine, N,N'-tetramethylethylenediamine, diethylenetriamine, triethylenetetramine, tetraethylenepentamine, pentaethylenehexamine, 1,1,4,7,7-pentamethyldiethylenetriamine, 1,1,4,7,10,10-hexamethyltriethylenetetramine and triethoxytriethyleneamine; cyclic polyamines such as cyclam and cyclen; heterocyclic compounds such as pyridine, pyrrolidine, piperidine, morpholine, N-methylpyrrolidine, N-methylpiperidine, N-methylmorpholine, tetrahydrofuran, tetrahydropyran, 1,4-dioxane, oxazole, thiazole and oxathiolane; β-ketoesters such as acetoacetic acid methyl ester, acetoacetic acid ethyl ester, and acetoacetic acid-2-methoxyethyl ester; and β-diketones such as acetylacetone, 2,4-hexanedione, 2,4-heptanedione, 3,5-heptanedione and dipivaloylmethane. These stabilizers are used in an amount of from 0.1 mol to 10 moles and preferably from 1 to 4 moles, with respect to 1 mole of the precursors.

The material for forming a thin film of the present invention is designed to reduce the components of impurity metal elements, impurity halogen such as impurity chlorine, and organic impurities, except for components constituting the material to a minimum. The amount of the impurity metal elements is preferably 100 ppb or less per element and more preferably 10 ppb or less. The total amount of the impurity metal elements is preferably 1 ppm or less and more preferably 100 ppb or less. For use as a gate insulating film of LSIs, the amount of alkali metal elements, alkaline earth metal elements, and the family elements (titanium, zirconium and hafnium) which have an effect on the electrical properties of the resulting conductive thin film is required to be minimized. The amount of the impurity halogen is preferably 100 ppm or less, more preferably 10 ppm or less, and still more preferably 1 ppm or less. The total amount of the organic impurities is preferably 500 ppm or less, more preferably 50 ppm or less, and still more preferably 10 ppm or less. Further, since water develops particles in the material for CVD or in the course of the CVD process, water is desirably removed from the metal compounds, organic solvents, and nucleophilic reagents used in the present invention to reduce the water content of each material as much as possible before use. The water content is preferably 10 ppm or less and more preferably 1 ppm or less.

Further, in order to reduce or prevent particle contamination in a thin film produced, in the material for forming a thin film of the present invention, as measured with a light scattering type liquid-borne particle sensor in a liquid phase, preferably the number of particles having a diameter of 0.3 µm or larger is 100 or less per 1 ml of the liquid phase; more preferably the number of particles having a diameter of 0.2 µm or larger is 1,000 or less per 1 ml of the liquid phase; and still more preferably the number of particles having a diameter of 0.2 µm or larger is 100 or less per 1 ml of the liquid phase.

The method for producing a thin film according to the present invention is a CVD process in which the vapor obtained by vaporizing the metal alkoxide compound of the present invention represented by the general formula (1) and the other precursors optionally used is introduced, optionally with a reactive gas optionally used, over a substrate; and these precursors are decomposed and/or chemically reacted in order to grow and deposit a thin film on the substrate. There are no particular limitations on transport and supply methods of the material, deposition methods, production conditions, production apparatus and others, but generally known methods and conditions may be applied.

The aforementioned reactive gas optionally used may include oxygen, ozone, nitrogen dioxide, nitrogen monoxide, water vapor, hydrogen peroxide, formic acid, acetic acid and acetic anhydride as an oxidative reactive gas; and hydrogen as a reducing reactive gas; and further, as a reactive gas used for nitride production, organic amine compounds such as monoalkylamine, dialkylamine, trialkylamine and alkylenediamine, hydrazine, ammonia, nitrogen and the like are mentioned.

In particular, in the case of producing the thin film that contains a metal oxide derived from the metal alkoxide compound of the present invention, the foregoing oxidative reactive gas, especially a reactive gas containing oxygen and/or ozone, is preferably used.

As the aforementioned transport and supply methods, there may be mentioned the aforementioned gas carrier methods, liquid carrier methods, cocktail source processes, single source processes, and others.

The aforementioned deposition methods include the thermal CVD process in which material gas or material gas and reactive gas are reacted only by heat in order to deposit a thin film; the plasma CVD process in which heat and plasma are used; the photo-excited CVD process in which heat and light are used; the photo and plasma-excited CVD process in which heat, light and plasma are used; and the ALD (Atomic Layer Deposition) process in which the CVD reaction is separated into elementary steps and deposition is carried out step by step in a molecular level.

The aforementioned production conditions include reaction temperature (substrate temperature), reaction pressure, deposition rate and the like. The reaction temperature is preferably 180° C. or higher at which the metal alkoxide compound of the present invention is sufficiently reacted and more preferably from 250° C. to 800° C. The reaction pressure is preferably from atmospheric pressure to 10 Pa for the thermal CVD and photo-excited CVD processes, and when plasma is used preferably from 2,000 Pa to 10 Pa. The deposition rate may be controlled by the supply conditions (vaporization temperature and vaporization pressure) of the material and the reaction temperature and pressure. At a high deposition rate, the resulting thin film possibly has poor properties; at a low deposition rate, there may be a problem with the productivity. Therefore, the deposition rate is preferably from 0.5 to 5,000 nm/min and more preferably from 1 to 1,000 nm/min. In the ALD process, an intended thickness is obtained by controlling the repetition number.

Further, the method for producing a thin film according to the present invention may include an annealing treatment under an inert atmosphere, an oxidative atmosphere or a reducing atmosphere in order to attain still more excellent electrical properties after an objective thin film is deposited. The method may also include a reflow treatment when steps are required to be embedded. The reflow temperature is from 400 to 1,200° C. and preferably from 500 to 800° C.

The thin film, that is produced by the method for producing a thin film according to the present invention employing the material for forming a thin film of the present invention, may be formed into a desired kind of thin film of metals, alloys, oxide ceramics, nitride ceramics, carbides, glasses and the like by selecting precursors of the other elements, reactive gases, and production conditions as appropriate. The composition of the thin film thus produced includes an oxide of Group 4 elements such as titanium oxide, zirconium oxide and hafnium oxide; a complex oxide of silicon and a Group 4 element; a complex oxide of a Group 4 element and aluminum; a complex oxide of a Group 4 element and a rare-earth element; a complex oxide of silicon, a Group 4 element and aluminum; a complex oxide of silicon, a Group 4 element and a rare-earth element; titanium nitride; zirconium nitride; hafnium nitride; a nitride oxide of silicon and a Group 4 element (HfSiON); and the like. These thin films are used as an electronic component member such as a high-dielectric capacitor film, a gate insulating film, a gate film, a ferroelectric capacitor film, a capacitor film, and a barrier film; and an optical glass member such as an optical fiber, an optical waveguide, an optical amplifier and an optical switch.

EXAMPLE

The present invention will be further described in detail with reference to the following examples, evaluation examples and comparative examples. However, the present invention is in no way limited to those examples.

Example 1

Production of Compound No. 9

In a dry argon gas atmosphere, 0.272 mol of zirconium tetrachloride and 200 ml of dry hexane were charged in a reactor flask; a solution dissolving 1.20 moles of diethylamine in 150 ml of dry hexane was added dropwise while keeping the liquid temperature below −10° C., and then the solution was stirred for 3 hours at −10° C.; and into the solution a mixture of 125 ml of 2-methyl-3-butene-2-ol and 100 ml of dry hexane was added dropwise while keeping the liquid temperature below −10° C., and then the solution was stirred for 18 hours at room temperature and further stirred for 5 hours at 50° C.; the filtrate obtained by removing the solid phase from the resulting reaction solution by filtration was concentrated and distilled under reduced pressure. A colorless transparent liquid was obtained from the fraction at a pressure of 0.17 to 0.18 torr and a vapor temperature of 83 to 95° C. The resulting colorless transparent liquid was identified as an objective compound No. 9 (Yield: 54.6%). The compound No. 9 was identified by elemental analysis and $^1$H-NMR. Further, the obtained compound No. 9 was subjected to the following vapor pressure measurement. The results were shown below.

(1) Elemental Analysis (Metal Analysis: ICP-AES)
   Zr: 20.8 mass % (theoretical value: 21.13 mass %)
(2) $^1$H-NMR (Solvent: Heavy Benzene)
   The chart was shown in FIG. 1.
(3) Vapor Pressure Measurement
   The vapor temperature in the vicinity of the liquid surface was measured at a constant pressure that is kept during the measurement. Four vapor temperatures were measured at different constant pressures for Clausius-Clapeyron plot, which provided the following equation for the vapor pressure.

$$\text{Log } P(\text{Torr}) = 6.01 - 2308/T(K)$$

Example 2

Production of Compound No. 15

In a dry argon gas atmosphere, 0.136 mol of hafnium tetrachloride and 455 ml of dry hexane were charged in a reactor flask; a solution dissolving 0.60 mol of diethylamine in 150 ml of dry hexane was added dropwise while keeping the liquid temperature below −10° C., and then the solution was stirred for 3 hours at −10° C.; and into the solution a mixture of 62.5 ml of 2-methyl-3-butene-2-ol and 50 ml of dry hexane was added dropwise while keeping the liquid temperature below −10° C., and then the solution was stirred for 12 hours at room temperature and further stirred for 5 hours at 50° C.; the filtrate obtained by removing the solid phase from the resulting reaction solution by filtration was concentrated and distilled under reduced pressure. A colorless transparent liquid was obtained from the fraction at a pressure of 0.11 to 0.12 Torr and a vapor temperature of 80 to 79° C. The resulting colorless transparent liquid was identified as an objective compound No. 15 (Yield: 35.4%). The compound No. 15 was identified by elemental analysis and $^1$H-NMR. Further, the compound No. 15 was subjected to the following vapor pressure measurement. The results were shown below.

Figure 2:
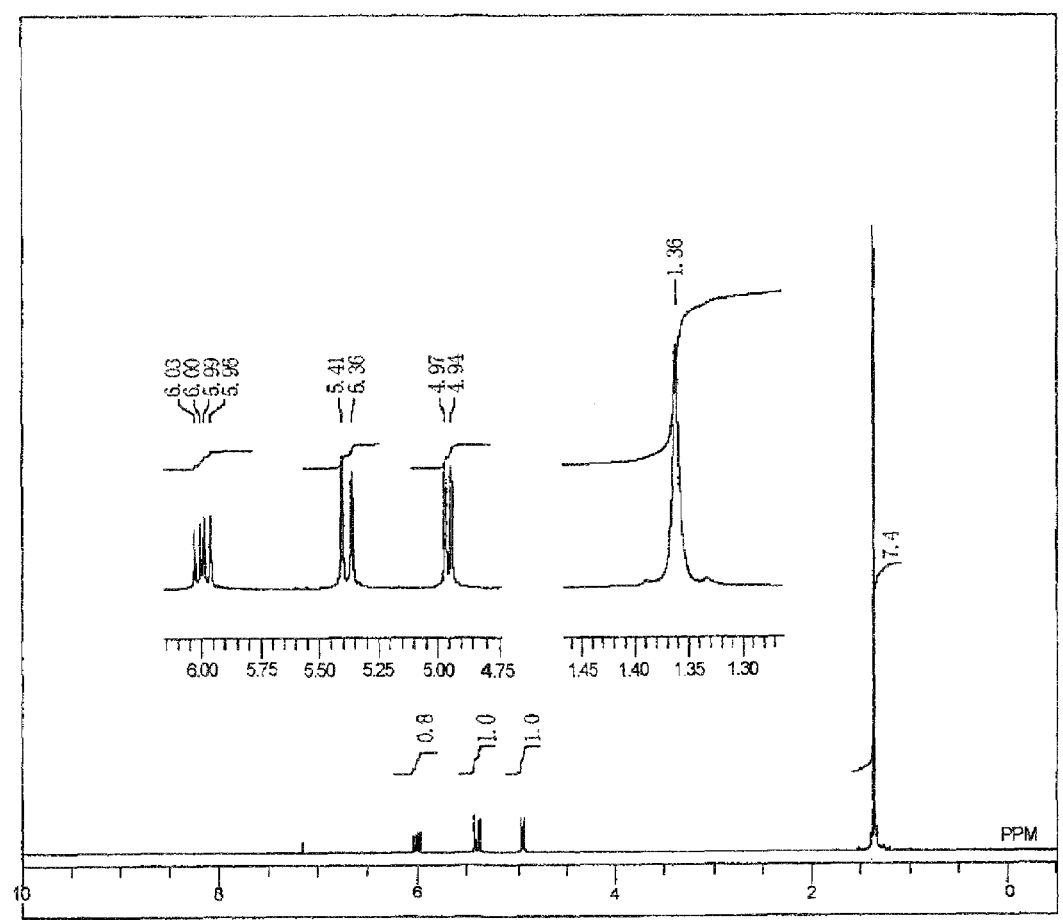
FIG. 2 shows the ¹H-NMR chart of the metal compound (compound No. 15) of the present invention obtained in Example 2.

(1) Elemental Analysis (Metal Analysis: ICP-AES)
   Hf: 33.9 mass % (theoretical value: 34.39%)
(2) $^1$H-NMR (Solvent: Heavy Benzene)
   The chart was shown in FIG. 2.
(3) Vapor Pressure Measurement
   The vapor temperature in the vicinity of the liquid surface was measured at a constant pressure that is kept during the measurement. Five vapor temperatures were measured at different constant pressures for Clausius-Clapeyron plot, which provided the following equation for the vapor pressure.

$$\text{Log } P(\text{Torr}) = 6.83 - 2641/T(K)$$

Evaluation Example 1

Evaluation of Thermal Stability

Thermal stability was evaluated for the compound No. 9 obtained in Example 1, the compound No. 15 obtained in Example 2, and comparative compounds of tetrakis(ethylmethylamino)zirconium, tetrakis(tert-butoxy)zirconium, tetrakis(ethylmethylamino)hafnium, and tetrakis(tert-butoxy)hafnium. After each compound was sealed with argon gas and kept for 1 hour at 160° C., 180° C. and 200° C., the compound was subjected to differential thermal analysis (TG) under the measurement conditions with a temperature elevation rate of 10° C./min from 30° C. in a dry argon gas stream (100 ml/min). The resulting 400° C. residue in mass % was compared for the evaluation. The results of the measurement are shown in the following Tables 1 and 2.

TABLE 1

| Compound | Residue at 160° C.(%) | Residue at 180° C.(%) | Residue at 200° C.(%) |
|---|---|---|---|
| Compound No. 9 | 0 | 0 | 1 |
| Tetrakis(ethylmethylamino)zirconium | 1 | 5 | 18 |
| Tetrakis(tert-butoxy)zirconium | 0 | 0 | 0 |

TABLE 2

| Compound | Residue at 160° C.(%) | Residue at 180° C.(%) | Residue at 200° C.(%) |
| --- | --- | --- | --- |
| Compound No. 15 | 0 | 0 | 0.5 |
| Tetrakis(ethylmethylamino)hafnium | 0 | 2 | 10 |
| Tetrakis(tert-butoxy)hafnium | 0 | 0 | 0 |

Evaluation Example 2

Evaluation of Oxidation Decomposition Property

Figure 3:
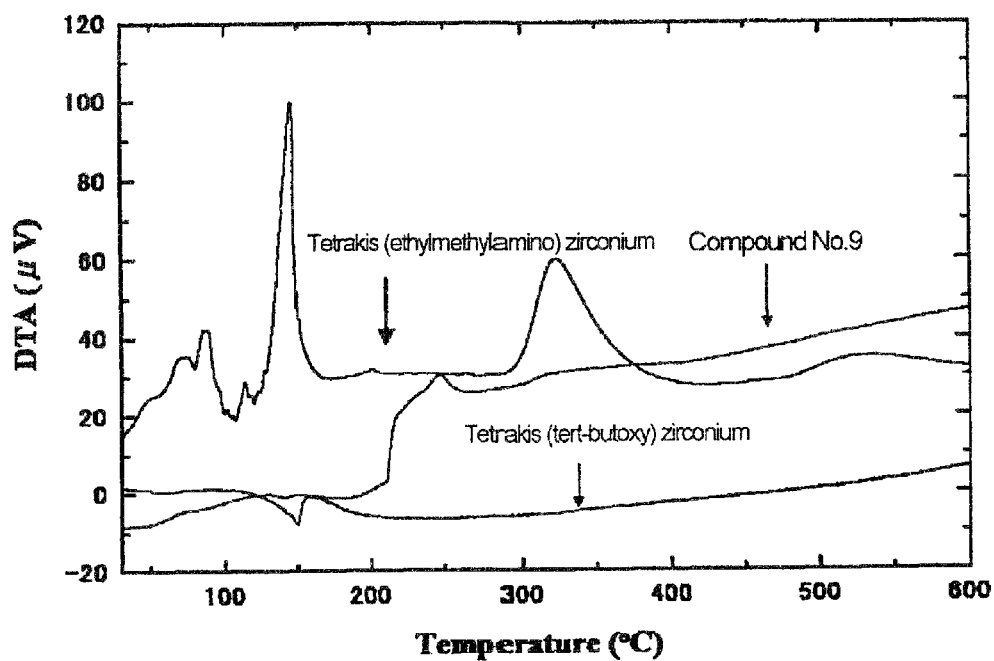
FIG. 3 shows the measurement results of differential thermal analysis (DTA) for the metal compound (compound No. 9) of the present invention, and the comparative compounds of tetrakis(ethylmethylamino)zirconium and tetrakis(tert-butoxy)zirconium.
Figure 4:
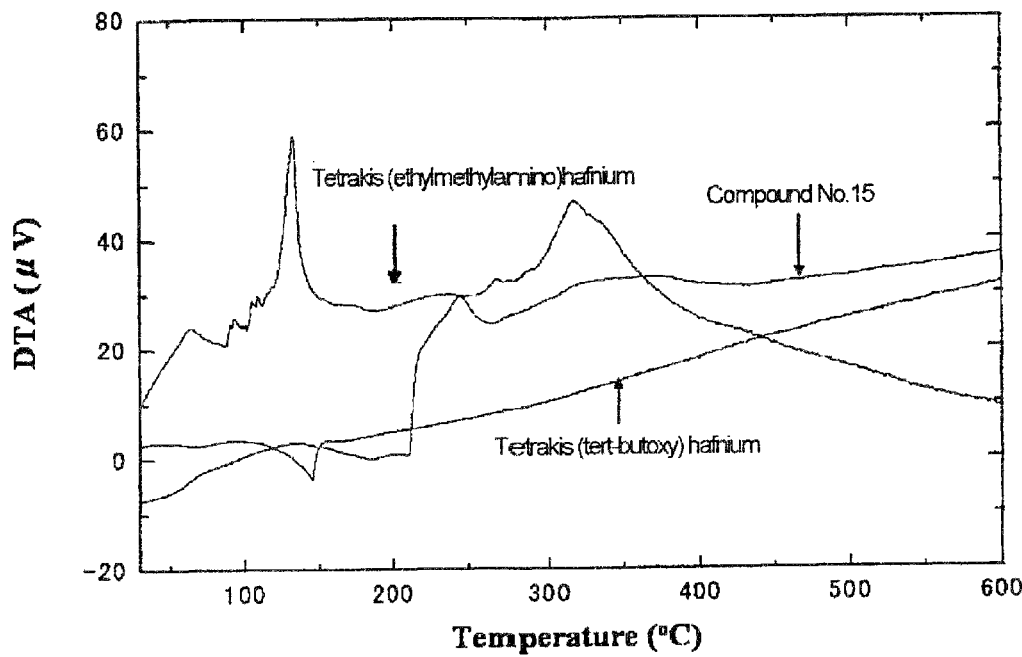
FIG. 4 shows the measurement results of differential thermal analysis (DTA) for the metal compound (compound No. 15) of the present invention, and the comparative compounds of tetrakis(ethylmethylamino)hafnium and tetrakis(tert-butoxy)hafnium.

Thermal oxidation decomposition property was evaluated for the compound No. 9 and No. 15 compound No. 15 obtained in the above Examples, and comparative compounds of tetrakis(ethylmethylamino)zirconium, tetrakis(tert-butoxy)zirconium, tetrakis(ethylmethylamino)hafnium, and tetrakis(tert-butoxy)hafnium. Each compound was subjected to differential thermal analysis (DTA) under the measurement conditions with a temperature elevation rate of 10° C./min from 30° C. in a dry oxygen gas stream (100 ml/min). The results of the analysis are shown in FIG. 3 and FIG. 4.

In the above Evaluation Examples 1 and 2, the compound No. 9 and compound No. 15s of the present invention were observed not to decompose at 160° C. and 180° C., and to decompose slightly at 200° C. Further, in oxygen, the compound No. 9 was observed to generate exothermic heat caused by oxidation decomposition at 215° C. to 270° C., and the compound No. 15 was observed to generate exothermic heat caused by oxidation decomposition at 220 to 270° C. The comparative compounds of tetrakis(ethylmethylamino)zirconium and tetrakis(ethylmethylamino)hafnium in argon were observed to decompose slightly at 160° C. and to decompose at 180° C. Further, in oxygen, oxidation decomposition started around room temperature, and exothermic reaction was observed at 130° C. to 170° C. and 295° C. to 395° C. The comparative compounds of tetrakis(tert-butoxy)zirconium and tetrakis(tert-butoxy)hafnium in argon were observed not to thermally decompose at 200° C. Furthermore, no decomposition was observed in the evaluation even after 1 hour heating at 240° C. In oxygen, no exothermic heat caused by decomposition was observed.

The results of the above Evaluation Examples 1 and 2 indicate that tetrakis(ethylmethylamino)zirconium and tetrakis(ethylmethylamino)hafnium, which are both tetrakis-dialkylamide compounds, are difficult to control their oxidation reaction because they are thermally unstable and excessively sensitive to oxygen.

Further, tetrakis(tert-butoxy)zirconium and tetrakis(tert-butoxy)hafnium, which are both tetrakis-alkoxide compounds, are thermally stable and also stable against oxidation decomposition, and indicate that they have a low productivity when used as a precursor for thin films containing metal oxides.

The compound No. 9 and compound No. 15, which are both the metal alkoxide compounds of the present invention, are thermally stable at least until 180° C., and are easy to control the process for producing thin films of metal oxides because the oxidation decomposition starts from 215° C. and indicate that they have an excellent productivity.

Example 3

Production of Zirconium Oxide Thin Film by Gas Transfer Process

Figure 5:
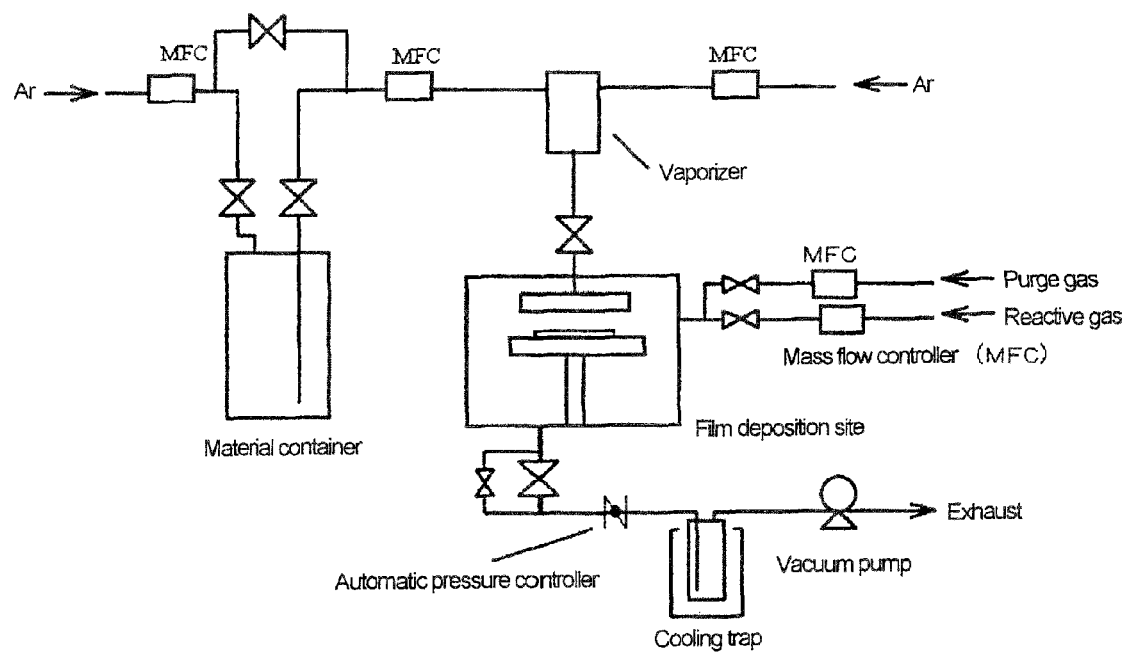
FIG. 5 is a diagrammatic illustration of an exemplary CVD apparatus used in Examples that is used in the method for producing a thin film of the present invention.

By using the compound No. 9 obtained by Example 1 and a CVD apparatus shown in FIG. 5, a zirconium oxide thin film was deposited on a silicon wafer under the following conditions with the following processes. When the measurement of film thickness and composition identification of the resulting thin film were carried out with the help of fluorescent X-rays, the film thickness was 10 nm and the film composition was zirconium oxide.

Conditions

Reaction temperature (substrate temperature): 280° C.

Reactive gas: ozone

Processes

The cycle consisting of a series of the following steps (1) to (4) was repeated 7 times, and at the end, the resulting thin film was annealed at 600° C. for 3 minutes.

(1) The vapor of compound No. 9 that was produced by vaporizing the compound No. 9 at a vaporization chamber temperature of 170° C. and a vaporization chamber pressure of 700 Pa to 800 Pa, was introduced and deposited at a pressure of 700 to 800 Pa for 1 second.

(2) Unreacted materials were removed by applying an argon gas purge for 2 seconds.

(3) A reactive gas was introduced and reacted at a pressure of 700 to 800 Pa for 1 second.

(4) Unreacted materials were removed by applying an argon gas purge for 2 seconds.

Example 4

Production of Zirconium Oxide Thin Film by Liquid Transfer Process

A 0.2 mol/L solution of the compound No. 9 serving as a material for CVD was prepared using dehydrated ethylcylohexane with a water content of less than 1 ppm. A zirconium oxide thin film was deposited on a silicon wafer with a CVD apparatus shown in FIG. 5 under the following conditions. When the measurement of film thickness and composition identification of the resulting thin film were carried out with the help of fluorescent X-rays, the film thickness was 10 nm and the film composition was zirconium oxide.

Conditions

Material: an ethylcyclohexane solution of the compound No. 9 (0.2 mol/L)

Material flow rate: 2.0 sccm

Vaporization chamber temperature: 170° C.

Reactive gas: oxygen at 200 sccm

Reaction pressure: 700 to 800 Pa

Reaction temperature (substrate temperature): 300° C.

Deposition time: 2 minutes

Annealing: in an oxygen gas atmosphere at 600° C. for 3 minutes

From the results of Examples 3 and 4, it was confirmed that a thin film production in which the deposition rate and the thin film composition were stably controlled are possible by using the material for forming thin films of the present invention.

INDUSTRIAL APPLICABILITY

The novel metal alkoxide compound of the present invention may be used not only as a material for forming thin films involving a vaporization step, but also as a material for forming thin films for MOD processes including coating thermal decomposition and sol-gel processes, an organic synthesis catalyst, a polymer synthesis catalyst and the like.

What is claimed is:

1. A metal alkoxide compound represented by the following general formula (1),

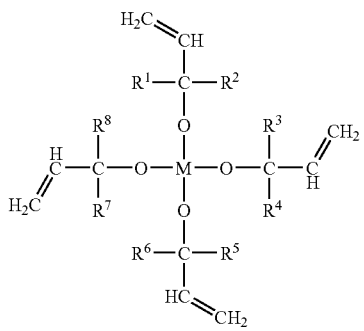
(1)

wherein, each of $R^1$ to $R^8$ is a methyl group; and

M is a titanium, a zirconium or a hafnium atom.

2. The metal alkoxide compound according to claim 1, wherein M is a zirconium atom.

3. The metal alkoxide compound according to claim 1, wherein M is a hafnium atom.

4. A material used for forming a thin film comprising the metal alkoxide compound according to claim 1.

5. A material used for forming a thin film comprising the metal alkoxide compound according to claim 2.

6. A material used for forming a thin film comprising the metal alkoxide compound according to claim 3.

* * * * *